(12) United States Patent
Stuttler

(10) Patent No.: US 6,580,448 B1
(45) Date of Patent: Jun. 17, 2003

(54) PROCESS AND DEVICE FOR THE PARALLEL CAPTURE OF VISUAL INFORMATION

(75) Inventor: Herbert M. Stuttler, Rankweil (AT)

(73) Assignee: Leica Microsystems AG, Wetzlar (DE)

( * ) Notice: Subject to any disclaimer, the term of this patent is extended or adjusted under 35 U.S.C. 154(b) by 703 days.

(21) Appl. No.: 08/930,100

(22) PCT Filed: May 13, 1996

(86) PCT No.: PCT/EP96/02046

§ 371 (c)(1),
(2), (4) Date: Jan. 16, 1998

(87) PCT Pub. No.: WO96/36271

PCT Pub. Date: Nov. 21, 1996

(51) Int. Cl.[7] .............................................. H04N 13/02
(52) U.S. Cl. ....................................................... 348/46
(58) Field of Search .............................. 348/42, 43, 45, 348/46, 47, 53, 61, 67, 114, 115, 54; 358/88; 351/208, 209, 210, 211; H04N 13/02

(56) References Cited

U.S. PATENT DOCUMENTS

| | | | |
|---|---|---|---|
| 3,170,979 A | | 2/1965 | Baldwin et al. .................. 88/1 |
| 4,582,403 A | | 4/1986 | Weinblatt .................... 351/210 |
| 4,751,570 A | * | 6/1988 | Robinson ...................... 358/88 |
| 4,879,596 A | * | 11/1989 | Miura et al. ................... 358/88 |
| 5,093,567 A | * | 3/1992 | Staveley ....................... 250/221 |
| 5,175,616 A | * | 12/1992 | Milgram et al. .............. 358/88 |
| 5,341,181 A | | 8/1994 | Godard ........................ 351/210 |
| 5,345,281 A | * | 9/1994 | Taboada et al. ............. 351/210 |
| 5,357,293 A | * | 10/1994 | Umori et al. ................ 351/209 |
| 5,360,971 A | * | 11/1994 | Kaufman et al. ........... 250/221 |
| 5,394,517 A | * | 2/1995 | Kalawsky .................... 395/129 |
| 5,649,061 A | * | 7/1997 | Smyth ........................... 395/20 |
| 5,703,637 A | * | 12/1997 | Miyazaki et al. ............. 348/53 |
| 5,781,165 A | * | 7/1998 | Tabata ............................ 345/8 |
| 5,875,018 A | * | 2/1999 | Lamprecht ................... 351/208 |
| 6,003,991 A | * | 12/1999 | Viirre ........................... 351/206 |

FOREIGN PATENT DOCUMENTS

| | | | | |
|---|---|---|---|---|
| DE | A-29 37 891 | | 4/1980 | ............ A61B/3/10 |
| DE | A-43 37 098 | | 5/1994 | ............ A61B/3/08 |
| EP | A-665 686 | | 8/1995 | .......... H04N/5/232 |
| WO | WO-A-94/17636 | | 8/1994 | ............ H04N/7/18 |

* cited by examiner

Primary Examiner—Chris Kelley
Assistant Examiner—Tung Vo
(74) Attorney, Agent, or Firm—Hodgson Russ LLP

(57) ABSTRACT

In order to ascertain what a person really sees, a monitoring, picture recording system has at least one video camera (3) arranged in such a way that the captured images at least approximately match the field of vision observed by the person. For that purpose, at least one eye parameter, such as the viewing direction and/or the refractive power of at least one eye (2), is determined and the picture recording monitoring system (3) is controlled depending on the thus determined parameters. The position of the center of the pupil is determined by image sensors (4) associated to the eyes and the visual axis is derived therefrom. At least one video camera (3) secured in an adjustable manner to the head is oriented according to the visual axes. Focusing may also be adjusted depending on the refractive power of the eye. The parallel capture of visual information may be used in many fields, in particular for monitoring tasks and also for therapeutic uses.

34 Claims, 2 Drawing Sheets

PROCESS AND DEVICE FOR THE PARALLEL CAPTURE OF VISUAL INFORMATION

BACKGROUND OF THE INVENTION

Figure 1:
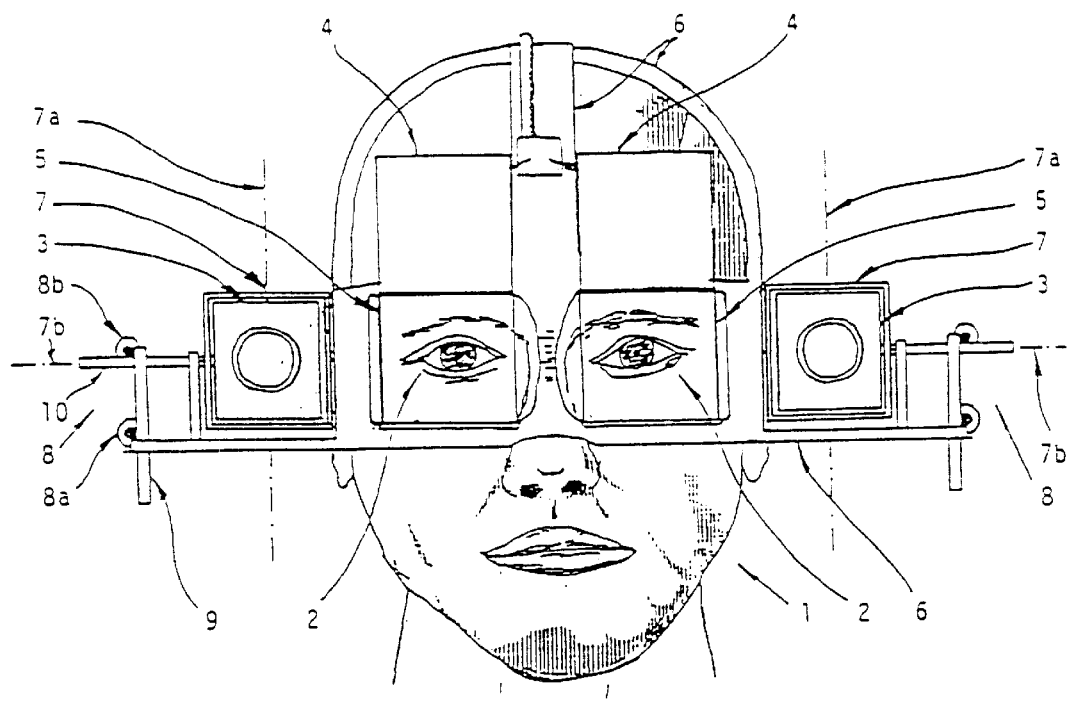

The invention concerns a process for collecting and recording visual information in parallel with an initial stereoscopic sensor system recording optical information, for instance the eyes of a person, and a device for carrying out such a process.

In manual activities which must be carried out extremely accurately, the result depends strongly on accurate observation during the activity. This is particularly the case for surgery on human or animal bodies. If the person operating does not observe the tissue in the vicinity of the knife accurately enough, there is a danger that an important structure such as a nerve bundle will be severed.

In systems with high hazard potential, such as nuclear power plants, assembly and checking must be done very accurately with good visual observation. Accurate observation is also essential in manipulations and tests during space flight, flying, and in complex terrestrial systems.

The desire to make what a person sees recordable is old, and until now it has not been possible to accomplish it. The attempt to obtain image information by sampling from the optic nerve does not take us to that objective because a significant portion of the signal processing and image collection occurs only in the brain.

One or more video monitoring cameras recording the whole area that can be examined by a person only show what is available, but not what the observing person sees. In order to be able to analyze potentially incorrect action of the person, it is certainly convenient if monitoring cameras record all that is visible. In addition, though, it is necessary to determine what is seen by the person observed.

A microscope headpiece which can be worn during surgery is known from U.S. Pat. No. 4,395,731. The operating field is monitored by two video camera placed in front of the eyes. The images from the video cameras are sent to monitors or image areas immediately in front of the eyes. Use of zoom optics makes it possible to magnify segments of the operating field.

The eyes always remain directed to the image source (e.g., a CRT). That can quickly lead to fatigue. It is also impossible to determine how the eyes comprehend the image provided to them. It could be that an important image area in the image source is never realized as such unless it falls on the portion of the retina that allows sharp vision. The focusing and alignment of the two cameras fixes the distance required between the cameras and the surgical field in order to get a sharp view with proper perspective. If this distance changes because of head movements, the images shown on the monitors can be unsharp, and/or may not be viewed by the eyes in such a way as to give a three-dimensional image. The ability for manual adjustment is hardly suitable for matching the orientation of the cameras to short-term changes in distance. Another disadvantage of the microscope headpiece is the limitation of the field of view by the camera optics and by the limited size of the monitors. Furthermore, changes in the field of view through movement of the eyes on the image area of the cameras or monitors are limited. An optical system which attempts to determine the observations of the operating or controlling person in which the person sees only the images from the cameras severely limits the ability of this person to observe and does not show what areas of the images provided are being looked at.

SUMMARY OF THE INVENTION

The objective of the invention is to determine what image information is actually seen by a person, or by any light-sensitive sensor system.

The solution according to the invention provides an image-recording control system, itself known from U.S. Pat. No. 5,341,181, acting in parallel with the eyes of the person or in parallel with a light-sensitive sensor system, the information record of which is made to coincide at least approximately such that at least one optical parameter of the eyes of or the image-recording initial system is determined and the corresponding optical parameter of the control system is adjusted in dependence on it. However, as the known system from the U.S. Patent is limited to a single control system which does not operate stereoscopically, the optogeometric determination of the image seen is only approximate. In contrast, according to the invention, an optical system is used which determines the stereo base (generally the interpupillary distance) and uses the directions of the fixation lines of the eyes to determine the fixation point. If the fixation point is known, the parallel observation of the working or controlling person is accomplished more accurately than in the system according to U.S. Pat. No. 5,341,181. Each new eye position is determined. The optical axes are preferably determined in a coordinate system which is fixed in relation to the head and which therefore moves with the head. As the movements of each eye are produced by six external eye muscles, it is possible to provide a sensor means which determines the stimuli to these muscles and derives from those the current eye position or the optical axes of the eyes.

Now the eye positions, or the directions of the visual axes, which are known in a coordinate system linked to the head, are used to control the directions of at least one, but preferably two cameras, through a mount connected with the head. The at least one camera is then connected with the head so that it can, like the eyes, carry out not only movements due to head movements but also movements relative to the head. It is apparent that an adjustable optical imaging system, especially one with adjustable mirrors or the like, can be provided to adjust the solid angle region being imaged in place of camera movement. Potential applications arise from quite different areas. One such area is that of video telephony, in which one of the speakers can observe the same thing, to a certain extent, with the eyes of the user, without added technical recording manipulations being required. In one preferred embodiment, cameras with CCDs are placed at the temple areas at both sides of the head. Each camera is assigned to the nearer eye. A mounting system, in particular, a kind of gimbal mount which makes camera movements possible is provided on a holder part which can be placed on the head, and an actuating means is provided. A camera, or its optical axis, is moved, for instance, by the movement of a rod which runs parallel with the camera axis and is connected to the camera. The rod is moved in a plane orthogonal to the rod by means of two linear drives arranged essentially perpendicularly to the rod.

As the camera positions are somewhat displaced from the eye positions, a geometric correction must be taken into consideration for control of the camera direction. This correction should assure that the two camera axes intersect at the same point as the intersection of the two visual axes of the eyes. No correction is needed for parallel visual axes.

In order to determine the fixation point of the eyes, it must be taken into consideration that the line of fixation of the eye does not coincide with the optical axis. The optical axis of the eye is the axis that is essentially symmetrical in rotation with respect to the optical structure of the eye (cornea, iris, lens). But because the most sensitive region of the retina, the *Fovea centralis*, is somewhat to the side of that axis, the line of sight or line of fixation is angled somewhat with respect to the optical axis. The deviation between these two lines can be considered as a standard difference, or it can be determined by fixing the eyes on a point of known position with a specified head orientation, and then measuring the directions of the visual axes of the eyes. From the known head direction, or the positions of the eyes and of the specified point of fixation, fixation lines are constructed so that the deviations between the visual axes and the corresponding fixation lines can be determined.

On consideration of the different directions of the visual axes and the line of sight of an eye, it is possible to calculate the direction of the visual axes by means of the sensors from the known deviation in the direction of the fixation line. Then the camera axes are aimed at the fixation point according to the directions of the line of fixation, so that the point of fixation lies in the center of the image area. But if the cameras are aimed according to the visual axes, the fixation point is somewhat to the side of the center of the image. The position of the point of fixation can than be marked or taken into consideration on the basis of the known deviations in the presentation or evaluation of the test images.

If the control observation system need not collect three-dimensional image information, an embodiment with only one camera is sufficient. It is preferably placed in the forehead region between the two eyes. This camera should also be aimed at the intersection of the visual axes or, if necessary, at the intersection of the lines of sight. In the absence of an intersection, the direction should be parallel to the visual axes.

Instead of aiming at least one camera, it is possible to use a camera solidly connected to the head, preferably directed forward, especially a camera with a wide-angle optical system. Then the fixation line derivable from measurement of the optical axis directions can be used to determine the area of the image being looked at. By continuously marking the current fixation point or by showing only an area of the image around the current fixation point, it is possible to determine what the person being observed is looking at.

Processes and devices to determine the direction of the optical axes of the eyes are known from the field of photographic and video cameras. Automatic focusing on the image area being looked at follows from the axial relations determined. To determine the axes, the eye is illuminated with infrared light, which is not perceived by the eye, and the reflected infrared light, or the image of the eye, is imaged on an image sensor plane. The eye image is made up essentially of reflections from the cornea and the iris. As most of the infrared light which passes through the pupil is not reflected back, the image sensor and an image evaluation unit connected to it can detect a difference in the boundary region between the pupil and the iris. If necessary, the shape of the iris, dependent on the direction of the eye, is also determined and the center of the pupil is established as the point of intersection of the two principal axes found in the image of the elliptical or perhaps circular outer margin of the iris. Then the visual axis is the line passing through the center of the pupil and through the center of eye rotation, which must have been determined previously.

To determine the center of eye rotation, lines of fixation are determined successively for the eyes fixed on two known points of fixation, with fixed known head position and direction. The points of fixation are preferably two fiducial points solidly connected to the camera mount and to the sensors for determining the pupil position, so that the determination can be independent of the direction of the head. Then the center of eye rotation is essentially at the intersection of the fixation lines through the fixation points. As the center of eye rotation is on the optical axis of the eye, a correction must be applied to increase the accuracy of the determination because of the deviation between the fixation line and the optical axis of the eye, as described above. The distance between the centers of rotation of the two eyes is the same as the interpupillary distance. If both eyes are looking essentially straight and horizontally to the front, toward infinity, both irises will be imaged as circles on both image sensor planes. The distance between the centers of the pupils is the interpupillary distance, and the centers of the pupils each lie in a zero-deflection position. To orient the eyes parallel and straight to the front, independently of the head position, fiduciary points linked to the mounting can, if necessary, be placed in front of each eye. Then the eyes are directed parallel and to the front if both the fiduciary points assigned to the two eyes coincide in the images of both eyes.

The size of the pupil is known by determining the boundary region between pupil and iris. This pupil can if necessary also be used as a measured parameter to control the aperture of the control system, thus varying the light conditions like those in the eye. That is advantageous if one is more interested in the image actually perceived by the eye than in a potentially better image recorded by the camera (e. g., in medical applications). In order to have optimal light conditions for image recording in the control system, the aperture is adjusted automatically. Then the actual brightness and sharpness impression of the user is lost; this can be selectable if necessary.

In the process of determining the visual axes at the present state of the art, the infrared light reflected back by the eye is deflected laterally out of the beam path of the camera onto the image sensor by means of a semitransparent infrared mirror (dichroic mirror) which has very high reflectivity for infrared light and very low reflectivity for visible light. That assures that the view of the image plane of the camera is undisturbed. In the solution according to the invention, on the other hand, the eye does not look either through an ocular or onto an image-displaying surface, but directly onto the object. But in order to determine the axes, at least one infrared mirror must be provided in front of the eye, which diverts at least the infrared image of the eye onto an image sensor outside the field of view. If necessary, the infrared illuminating light is directed onto the eye from at least one source at the side through a mirror.

In the known applications of visual axis determination, the eye is always near the ocular of the viewfinder, so that the eye image determined by the infrared measurement is affected little if at all by reflections of ambient light. In the system according to the invention, the eye is exposed to the ambient light essentially without shielding. To prevent disturbance by ambient light of the image of the eye and its evaluation, published German Patent Application 43 37 098 A provides a mode of operation in which the image information based on the difference between phases with infrared illumination and ambient light and phases with only ambient light is evaluated. An extremely compact sensor for axis determination is known from European Patent Application EP 602 895.

As, in the system of the invention, the eye is exposed to ambient light essentially without limit, however, it is well illuminated and can if necessary allow determination of the pupil position with an image sensor (CCD) that is sensitive to visible light. Thus illumination with infrared light can be omitted for the axis determination.

Along with the direction of the eye, its accommodation by adjustment of the refractive power of the lens is another important parameter of the observation process. We can, in a first approximation, assume that the refractive power of both eyes is always adjusted to the fixation point. Correspondingly, the camera optical systems should be controlled so that the fixation point, the distance of which can be determined from the distance between the eyes and the directions of the fixation lines (triangulation) is focused sharply. Determination of the distance of the fixation point by triangulation is sufficiently accurate, at least in the near field. If necessary, the camera optical systems can also be focused sharply in the range of the fixation point by auto-focusing.

Eye refractors are used to determine the refractive power of the eye. They measure essentially the spherical dioptric power, the astigmatism, and the astigmatism axis. As the astigmatism and its axis do not change during an observation process, at least as a first approximation, only the spherical dioptric power need be measured to control the refractive power of the control system by means of measured parameters. The measurement of these parameters is made more difficult by the fact that it must be done for arbitrary directions of the eye.

The change of the refractive power of the lens involves changes in the shape of the lens. Those can be determined by means of ultrasound echography, at least in certain directions or sectioning planes. To measure the eye along the optical axis, an ultrasonic signal is coupled into the eye through a lead-in segment of water. The lens thickness is determined from differences in travel times of the echoes at the two edges of the lens. Aside from the pure travel time measurements along an axis, imaging ultrasound measurement processes are also used for the eye. They give cross-sections through the eye. In the system according to the invention the eye must have essentially unimpeded vision to the front. Any coupling in of ultrasound that may be required must therefore be done at the side of the eye. Then the form of the lens, from at least one cross section, along with the current visual axis, must be used to calculate the current refractive power.

Ultrasonic measurement has the advantage, compared to measurements with light, that the interior of the eye, including the lens, can be examined not only essentially along the optical axis but also in a direction in which the eye is transparent to light. However, the accuracy of measurement is poorer and the conversions that are needed are more time-consuming.

With the preferred optical measurement of the refractive power of the eye, it is important that the refractor be focused suitably for the eye being examined, and adjusted correctly for the distance between the eyes. It is also important to prevent the harmful effects of blinking on the measurement. A refractor which, in an initial step, is adjusted optimally for the eye being examined, which is directed at a fixation object, is known from the published German patent application DE 29 37 891 A. In another step, an adjustable test image structure, preferably light beams of definite directions, is imaged on the retina by the lens. The light reflected back out of the eye from the image on the retina, and its change on adjustment of the test image, is analyzed to determine the mean refractive power (spherical), the astigmatism (cylindrical) and the axis of astigmatism (cylinder axis).

When the eye is movable, and its optical axis is known from a measurement, it must be possible to image an infrared test image onto the retina along the current visual axis. That can be done, for example, by producing an image with a light-emitting diode array, or with a rear-illuminated liquid crystal display, which is deflected by an optical system, focused if necessary, and directed through the pupil into the eye. Imaging on the retina is done by deflection, again, and focusing of an image detection system or infrared sensors. The test images from various regions of the array, or from the display, can be directed onto the eye with suitable optics along the current optical axes and focused if necessary. The imaging action of the optical system of the eye can be determined by varying the test images. It is obvious that the optical elements in the free field of view of the eye, and especially the deflecting elements, or dichroic mirrors, the construction of which is known, for instance, from the. Japanese patent application JP 88865/1978, must be fully transparent for visible light. Not only flat mirrors but also curved mirrors may be used to deviate the beam. It is possible, in essence, to illuminate the eye from any possible direction of the visual axis from two opposite sides by means of two quarter-spherical mirrors.

With the measuring system described above, having a transmitter matrix and a receiver matrix, sequential transmission and parallel reception can be provided in place of transmission of test images. In this way, at least part of the light diodes in the diode array are turned on and off successively, and the back-scattered images are used, preferably along with the axial position, also determined, to determine at least one accommodation parameter. In particular, the pupil position and the axis position can be determined using a system with one transmitter and one receiver matrix.

In place of a light-emitting diode array, it is also possible to use an infrared diode laser which is adjustable in direction and, especially, in position. It must be possible to direct the laser beam, through an optical system and a dichroic superimposing element, essentially along the current visual axis for imaging on the retina. It must be possible to direct the back-scatter image from the retina, which is deflected out of the field of view and, if necessary, controlled by an adjustable optical system, to at least one infrared sensor or, if necessary, to a sensor array.

Continuous determination of the visual axes, the pupil diameter, and the accommodation during a viewing process makes it possible to collect image data in parallel with cameras and to perform a dynamic vision analysis with this image material. Accommodation errors can be detected by comparing the position of the fixation point with the measured refractive power or accommodation distance. By specifying fixation points which can be moved in three dimensions it is possible to examine how the eyes follow these points. Dynamic vision analyses can also detect errors in eye guidance in reading text or music, and in particular, in monitoring instrument displays. Aside from testing, control and diagnostic applications, therapeutic applications are also possible. Exercises in the boundary area of occurrence of recognized visual errors, especially accommodation limits or problems in exact aiming of both eyes at a single point (fusion problems) can be improved with interactive control of the visual activity. In music teaching, both good and poor reading of notes can be recorded and analyzed from the records. Optimizing the visual process can also be important in sports such as tennis, shooting, and games with goalkeepers. For instance, persons in a control center could give instructions directly to a user by radio, e. g., to fix on certain objects.

View control of menu fields on a display screen is another area of application of data collection according to the invention. This potential is particularly advantageous for operations in which the person operating follows the operation on an image screen. The menu fields are preferably labeled by symbols which are stored in the image processing system for the purpose of recognition. The segments of the control system image near the fixation point can be compared with the stored symbols using image processing. For this purpose, both the screen information and the image information from the control system are accessible for image processing. Now if the controlled user eyes fixate on a menu field, or its symbol, for longer than a predetermined time, or initiate the recognition process via a switch that can be actuated mechanically or acoustically, the symbol being viewed is assigned, if possible, to a corresponding stored symbol. If the assignment is successful, other menu fields can be presented on the screen, if necessary, or a command is issued, after confirmation if necessary.

View control of menu fields through an ocular is known, for instance, from the field of video cameras. There only one visual axis need be determined to recognize the image area being looked at, or to make an assignment. If the head and eyes are freely movable, the zero point position and the orientation of the coordinate system fixed to the head must be known, along with the visual axis, or the line of fixation, in the same coordinate system in order to specify a fixation line in three-dimensional space correctly and, if necessary, to be able to intersect with the image screen plane. Aside from determination of the visual axis, the motions of the head must be monitored telemetrically. The cost of specifying a fixation line in three-dimensional space is high and, at least with small menu fields there is a danger that the proper field will not be recognized. Comparison of the symbols seen with previously specified symbols may be simpler and more efficient in most cases.

Another application, basically similar to the view-controlled selection of menu fields described above, is the recognition of instrument displays being checked. In monitoring instruments, it is important that individual displays must be read at least once by the monitoring person in a specified time interval. The image material of the control system must, then, present this display at least once in the fixation region within the specified time interval. That can be controlled by image processing.

Another example application of the data collection according to the invention with an image-recording control system is view-control of the cursor on a screen being viewed. Instead of assigning stored symbols to image segments from the control system in the region of the fixation point by means of image processing, as described above, it is possible to provide coordinate marks on the screen being viewed, which can be detected in the image seen by means of image processing. The position of the fixation point or image center of the image of the screen recorded by the camera aimed according to the eye direction can then be converted to screen coordinates. The screen coordinates of the fixation point of the eyes, and, therefore, of the camera, are transmitted to the screen, or to its control system, so that the fixation point can be represented, by means of its coordinates, on the screen being viewed, in the form of a cursor.

View control of the cursor position on a screen being viewed has very many potential applications. In operations in which the operating person follows the operation on the screen, the view cursor can assist the orientation of persons assisting the operating person, making it easier for them to understand the process of the operation, or making explanations easier and making it easier to follow instructions. The view-controlled cursor can select menu fields, localize zoom regions, or even be controlled by movements of the recording system generating the image and, if necessary, by auxiliary devices.

It is obvious that the view control of the cursor can essentially replace all known cursor controls, even the widely-used mouse. This potential replacement is particularly advantageous for persons with severe physical disabilities. Even if only the eyes can be moved, view control of the cursor makes efficient and wide-ranging computer use possible.

In the eye, the resolving power is greatest for the part of the image formed on the *Fovea centralis*. Outside of this region, the resolution diminishes rapidly in all directions. It is actually vanishingly small in the region of the blind spot. The image picked up by a camera normally has essentially the same resolution over the entire image. Now, in order to produce the image information which the observer gets, the image information from the control system can be reduced toward the edges by means of image processing, taking into consideration the actual resolving power of the eye. If necessary, one can even place a soft-focus lens, which gives the desired resolution, on the control system camera. If the reduction in resolution is done only in the analysis of the recorded image, by means of image processing, then it is possible to compare the optimal observation with a real one, especially to determine what information is lost in the eye.

Such comparisons could be important in judging surgical malpractice cases, as there is generally negligence only in case there was an incorrect cut, the danger of which was detectable, or if an error was seen by the operating person without him or her reacting to it. Another imaging monitoring system, which produces images with a perspective different from that of the operating person and without the limitations of the human eye could provide image information not accessible to the operating person.

It is obvious that other image-processing steps can also be provided, such as emphasizing contour lines or introduction of masks. In this process, image material from other imaging sources can also be used to produce images. Damping processes for the camera motions in case of very rapid eye movements may be required, and filter processes may be provided for the images produced.

It may be necessary to process the image material in a way similar to the processing in the brain of the image recorded by the retina. Contrasts can be amplified, blurs sharpened, peripheral information filters, and movements of the head and the outside world compensated so as to produce a fixed image. Aside from the image material, the measured parameters may also be filtered and/or processed to make possible optimal control of the control system and thus optimal image recording.

Similarly, image-altering processing steps can be used to gain understanding of other visual behavior or capabilities. The image material from the control system is adapted, by image processing, to other vision, such as vision in case of retinal detachment, or the vision of animals, the eyes of which have other characteristics.

Aside from measurement of eye parameters and image recording by means of a control system, it is also possible to provide for images being directed to at least one eye by means of a semitransparent optical deflecting element. The images added can be derived from the control system and, if necessary in case one eye has a visual defect, show the image that could be seen with optimal vision. Conversely, a person with normal vision can be provided with the image material available to a person with defective vision.

In surgical operations, it would often be desirable to be able to provide the surgeon with images from other imaging processes, such as X-rays, ultrasonic images, computer tomograms and nuclear magnetic resonance images, especially if they could be overlaid on the visible surgical field. If necessary, an electronically switched shutter element could be provided behind (as seen from the eye) the deflecting element introducing the images. Such a switching element would, for example, change from a transmissive to a reflective state due to liquid crystal changes. In this way it is possible to superimpose the added images over the actual background, or to view them without the background.

The control system can, if necessary, include a zoom optical system so that, if required, a zoomed segment in the vicinity of the visual fixation point is observed. For example, superimposing the zoomed image can allow the operating person to switch from direct observation to observation of an enlarged subfield in delicate phases of the operation (comparable to the known microscopic headpiece). The directions of the eyes while looking at the zoomed image is preferably no longer used to move the optical axes of the cameras in the control system, but rather for menu-controlled selection of the parameters of the control system, rather as described in commonly owned U.S. patent application Ser. No. 08/817,634 filed Apr. 24, 1997 and claiming priority of Swiss Patent Application CH 3217/94-9 for surgical microscopes. If necessary, variations in the distance between the camera and the observed field are compensated by autofocus, and especially by small changes in camera direction.

Aside from picking up and, if necessary, superimposing in a zoom image, the control system can also collect images in a wavelength range outside the visible range, especially in the infrared range, or images with an enlarged field of view and/or with altered stereo base, and can, if necessary, provide them to the eyes.

The initial image-recording system is preferably at least one eye, especially a human or animal eye. Basically, though, all light-sensitive sensor systems, including, if necessary, even single sensors, systems with multiple sensors, and image recording systems with an image-recording control system can be controlled. It is preferable that at least one directional axis of the sensor system be included and that the at least one camera is aimed in dependence on that direction. Use of an image-recording control system to control a light-sensitive initial system makes possible control of the situation-dependent behavior of the initial system.

It is obvious that the image information from the control system and, if necessary, the parameters measured for the initial image-recording system can be recorded.

Other device claims are conceivable, analogous to the process claims, which exhibit concrete features with which the corresponding process steps can be carried out.

SUMMARY OF THE INVENTION

The drawings explain the invention by means of embodiments presented schematically. These embodiments do not limit the invention.

FIG. 1. Front view of a head with two video cameras placed laterally from the eyes and two sensors above the eyes to determine the visual axes.

Figure 2:
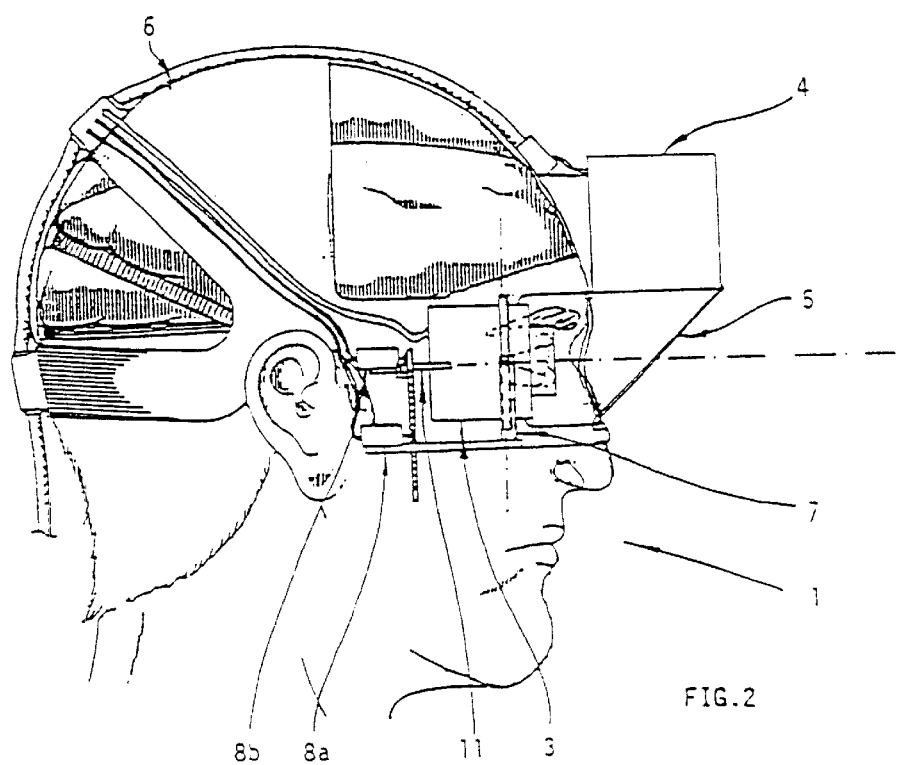

FIG. 2. Side view of a head with video camera, visual axis sensor, and deflecting mirror.

Figure 3:
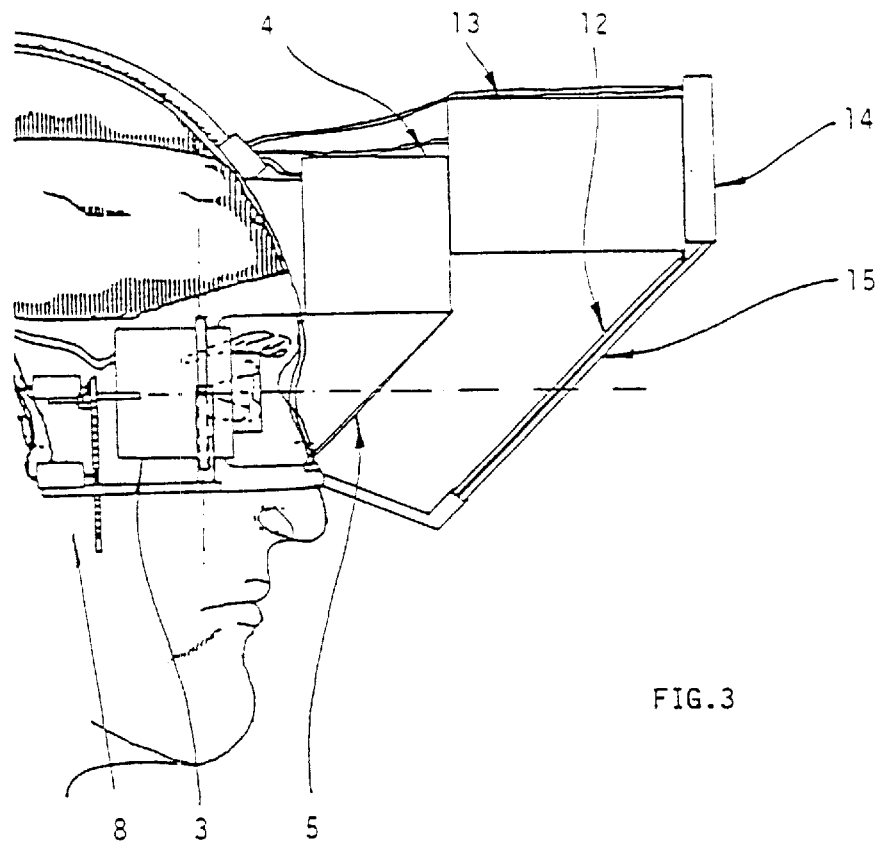

FIG. 3. Side view of a head with video camera, visual axis sensor, deflecting mirror, image superimposing means, and switchable shutter element.

Figure 4:
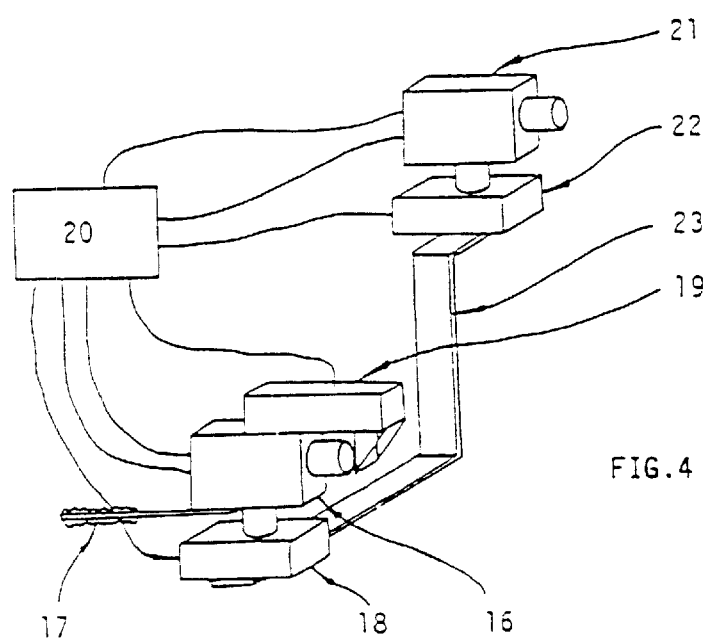

FIG. 4. View of a system with an initial camera which can be aimed manually, a control camera, and a means for measuring, controlling, and image recording.

DETAILED DESCRIPTION OF THE PREFERRED EMBODIMENTS

FIG. 1 shows a head 1 with two video cameras 3 placed laterally from the eyes 2 and two measuring systems above the eyes 2, which include eye-direction sensors 4, from the measurements or images from which it is possible to derive the positions of the centers of the pupils. In order to provide to the eyes 2 images from the aiming sensors 4 and, if necessary, light, especially infrared light from eye-direction sensors 4, initial semitransparent deflecting elements 5 or mirrors, preferably dichroic mirrors, are placed in front of both eyes. If necessary the measuring system also includes a sensor arrangement and a processing unit to determine the refractive index of each eye. The sensors 4, the semitransparent mirrors 5 and the cameras 3 are fastened to a mount 6 which can be placed upon the head 1.

It is preferable to provide gimbal mounts 7 as mounting devices for the cameras 3, with primary and secondary motion axes 7a and 7b which are essential perpendicular to each other. It is preferable, in order to aim the cameras 3 according to the measured visual axis parameter in desired directions relative to a coordinate system linked to the head, or to the mount 6, to provide a two-dimensional adjusting system 8 for each camera. The adjusting systems 8 actuate rearward camera extensions by means of two linear drives, 8a and 8b, an initial drive and a secondary drive, operating along axes 7a and 7b. Here the initial drive 8a is fastened to the holder 6 and moves a primary rod 9, at the end region of which the secondary drive 8b is fastened. The secondary drive 8b is connected to the camera extension through a secondary rod 10.

FIG. 2 shows the head 1 with the holder 6 from the side, so that the camera extension 11 can be seen. The side view also shows the mounting and orientation of the partially transparent mirror 5. The wires from the sensors 4, the adjusting systems 8 and the cameras 3 are preferably connected to a measuring, control and image-recording means. This control means assures the orientation matching the eye direction and/or the camera 3 focus corresponding to the measured refractive index of the eye. The control system also processes and/or stores the signals from the sensors 4 and the cameras 3.

FIG. 3 shows an embodiment in which, aside from measurement of the visual parameters and image recording by the cameras 3 adjusted to match the parameters measured, it can also be provided that at least one eye can be provided with images from an image source 13 fastened to the holder 6 through a second semitransparent optical deflecting element 12. In order both to superimpose the images on the background or to make only those images available to the eye, a shutter element is provided if desired, behind the deflecting element 12 as seen from the eye 2, which can be switched by an electronic unit 14. For instance, it changes from a transmissive to a reflective state due to liquid crystal changes. The control of the image source 13 and the unit 14 is provided from the control system.

FIG. 4 shows an embodiment in which the initial sensor system recording the image information and also the control system each includes at least one video camera. Instead of making the image viewed eye by one viewable, the control system is intended to view images parallel to an initial video camera. For this purpose, an initial video camera 16 is moved manually by means of a control handle 17. To determine the direction of the initial camera 16 it is provided with a direction-determining unit 18. The particular adjustment of the optical system of the initial camera is, if desired, made determinable either from the sensor from the optical adjusting system of the camera 16 or from the measuring means 19 mounted on camera 16.

The parameters measured for the initial camera 16 are transmitted to a control system 20 which controls a second camera 21 (specifically its aim and/or the adjustment of its optical system). The aiming is done by an aiming means 22 on which the second camera 21 is mounted. If necessary the mounts 18 and 22 of the two cameras 16 and 21 are connected together by a mounting system 23.

Applications in which the control system intentionally exhibits different parameters than the sensor system are also included within the range of the invention. For instance, the sensor system (e. g., video cameras in a robot) could work in a tele-zoom range, while the control system exerts an oversight function in the wide angle range. Thus it can also be advantageous that the control system works in a certain light wave range parallel to the sensor system, which works in a different light wavelength range.

What is claimed is:

1. A method for capturing image information parallel to the visual detection of image information by a pair of eyes, said method comprising the steps of:
   a) providing an image-recording system arranged in correspondence with said pair of eyes, and control means for changing the alignment of said image recording system;
   b) measuring a stereo base distance between said pair of eyes;
   c) measuring a respective alignment direction for each of said pair of eyes;
   d) establishing a fixation point of said pair of eyes based on said stereo base distance and said respective alignment directions; and
   e) aligning said image-recording system toward said fixation point to collect said image information.

2. The method according to claim 1, wherein at least one optical axis defined by at least one optical system is determined in measuring said respective alignment directions.

3. The method according to claim 1, wherein said pair of eyes comprises the eyes of a person.

4. The method according to claim 3, wherein said image-recording system is mounted on the head of said person.

5. The method according to claim 4, wherein said respective alignment directions are measured by a pair of eye direction sensors located in front of said eyes.

6. The method according to claim 1, wherein said image-recording system includes a camera, and said camera is aligned toward said fixation point.

7. The method according to claim 1, wherein said image-recording system includes a pair of cameras, and each of said pair of cameras is aligned toward said fixation point.

8. The method according to claim 3, wherein said image-recording system includes a pair of cameras, and each of said pair of cameras is aligned toward said fixation point.

9. The method according to claim 5, wherein each of said pair of eye direction sensors includes a dichroic mirror in front of an eye and imaging means out of the field of view of said eye, said dichroic mirror passing visible light to said eye along said alignment direction of said eye and reflecting infra-red light between said eye and said imaging means to form an image of said eye at said imaging means.

10. The method according to claim 9, wherein said imaging means is a CCD, and a position of the center of the pupil of said eye is determined in order to determine an optical axis of said eye.

11. The method according to claim 9, further including an adjustment step of directing said eyes at a reference point linked to said head to determine said stereo base distance.

12. The method according to claim 10, wherein said optical axis is established through the center of rotation of said eye and through the center of the pupil of said eye.

13. The method according to claim 3, wherein said step of establishing said fixation point includes determining a line of sight for each of said eyes from said respective alignment directions by means of an angular correction.

14. The method according to claim 13, wherein said angular correction is a standard angular correction for all persons.

15. The method according to claim 3, wherein said angular correction is a non-standard angular correction determined by fixing said eyes on a reference point of known position with a specified head orientation, measuring said respective alignment direction for at least one of said eyes, constructing said line of sight for said at least one eye, and calculating the angular difference between said measured alignment direction and said line of sight.

16. The method according to claim 8, further including the step of measuring a refractive power of at least one of said eyes, said refractive power including a spherical dioptric power of said at least one eye.

17. The method according to claim 16, wherein said refractive power further includes an astigmatism value and an astigmatism axis of said at least one eye.

18. The method according to claim 6, further including the step of adjusting a focus of said camera to a distance between said camera and said fixation point.

19. The method according to claim 7, further including the step of adjusting a focus of each of said pair of cameras to a distance between said camera and said fixation point.

20. The method according to claim 16, further including the step of adjusting a focus of each of said pair of cameras to a distance between said camera and said fixation point, wherein said focus is adjusted based on said measured refractive power.

21. The method according to claim 17, further including the step of adjusting a focus of each of said pair of cameras to a distance between said camera and said fixation point, wherein said focus is adjusted based on said measured refractive power.

22. The method according to claim 18, wherein said focus is adjusted automatically.

23. The method according to claim 19, wherein said focus is adjusted automatically.

24. The method according to claim 1, wherein said captured image information is recorded.

25. The method according to claim 16, wherein said refractive power is recorded.

26. The method according to claim 3, further including the step of directing images from an image source to at least one of said eyes through a semitransparent optical deflecting element positioned in front of said eye.

27. The method according to claim 26, wherein said image source is said image recording system.

28. The method according to claim 26, wherein said image source is an ultrasound image source.

29. The method according to claim 26, wherein said image source is an X-ray image source.

30. The method according to claim 26, wherein said image source is a computerized tomography image source.

31. The method according to claim 26, wherein said image source is a positron emission tomography image source.

32. An image recording system for capturing image information parallel to the visual detection of image information by a pair of eyes said image recording system comprising:

at least one camera arranged in correspondence with said pair of eyes, said at least one camera having an optical parameter in common with said pair of eyes;

control means for changing the alignment of said at least one camera and adjusting said optical parameter of said at least one camera;

means for continuously establishing a fixation point of said pair of eyes and providing signal information to said control means to align said at least one camera with said fixation point; and means for continuously determining said optical parameter of said pair of eyes and providing signal information to said control means to adjust said optical parameter of said at least one camera to be congruent with said optical parameter of said pair of eyes.

33. An image recording system according to claim 32, wherein said means for continuously establishing a fixation point includes at least one direction sensor for determining at least one optical axis of said pair of eyes.

34. An image recording system according to claim 32, wherein said means for continuously determining said optical parameter of said pair of eyes includes at least one refractive power detector for determining a refractive power of said pair of eyes, whereby the focus of said at least one camera is adjusted in accordance with said refractive power.

* * * * *